United States Patent [19]

Grethlein

[11] 4,237,226
[45] Dec. 2, 1980

[54] PROCESS FOR PRETREATING CELLULOSIC SUBSTRATES AND FOR PRODUCING SUGAR THEREFROM

[75] Inventor: Hans E. Grethlein, Hanover, N.H.

[73] Assignee: Trustees of Dartmouth College, Hanover, N.H.

[21] Appl. No.: 14,474

[22] Filed: Feb. 23, 1979

[51] Int. Cl.$^3$ .......................... C13K 1/02; C12P 7/18; C12P 7/24; C12R 1/885
[52] U.S. Cl. ...................................... 435/99; 127/29; 127/37; 435/105; 435/252
[58] Field of Search .................... 127/37, 29; 435/105, 435/252, 99

[56] References Cited

U.S. PATENT DOCUMENTS

| 2,086,701 | 7/1937 | Dreyfus | 127/37 |
|---|---|---|---|
| 2,284,500 | 5/1942 | Warth | 127/37 |
| 2,752,270 | 6/1956 | Specht | 127/37 |
| 2,900,284 | 8/1959 | Oshima | 127/37 |
| 2,945,777 | 7/1960 | Riehm | 127/37 |
| 3,067,065 | 12/1962 | Kusama | 127/37 |
| 3,212,933 | 10/1965 | Hess | 127/37 |
| 3,479,248 | 11/1969 | Nobile | 127/37 X |
| 3,523,911 | 8/1970 | Funk | 127/37 X |
| 3,642,580 | 2/1972 | Ghose | 435/105 |
| 3,663,369 | 5/1972 | Morehouse | 435/99 |
| 3,972,775 | 8/1976 | Wilke | 435/99 |
| 3,990,945 | 11/1976 | Huff | 435/99 |
| 4,023,982 | 5/1977 | Knduth | 127/37 X |
| 4,070,232 | 1/1978 | Funk | 127/37 |
| 4,160,695 | 7/1979 | Dietrichs | 127/37 |

OTHER PUBLICATIONS

Diane R. Knappert, Master of Engineering Thesis, "Enzymatic Hydrolysis by Trichoderma Cellulase," Dartmouth College, Hanover, N.H., Jun. 1978.
David R. Thompson, Master of Engineering Thesis, "Acid Hydrolysis as a Means of Converting Municipal Refuse to Ethanol", Dartmouth College, Hanover, N.H., Oct. 1977.

Primary Examiner—Sidney Marantz
Attorney, Agent, or Firm—Robert Shaw

[57] ABSTRACT

Processes for treating cellulosic substances prior to hydrolysis which lead to shortening hydrolysis time and to increasing sugar yield. As exemplary, an aqueous slurry of the cellulosic substance is acidified and heated to and maintained at a temperature to produce a change in the cellulosic structure; the heating period is controlled so that there is little glucose formation. The pretreated cellulose may be subsequently hydrolyzed by acid or enzyme.

34 Claims, No Drawings

PROCESS FOR PRETREATING CELLULOSIC SUBSTRATES AND FOR PRODUCING SUGAR THEREFROM

The Government has rights in this invention pursuant to a Grant awarded by the National Science Foundation.

The present invention relates to processes for the production of glucose and other sugars.

Attention is called to two theses: The master's thesis of David R. Thompson entitled "Acid Hydrolysis As A Means Of Converting Municipal Refuse to Ethanol: Process Kinetics And Preliminary Plant Design" (the work described in the Thompson thesis was done under supervision of the present inventor and there was a reduction to practice of concepts first proposed by the present inventor); and the master's thesis of Diane R. Knappert entitled "Partial Acid Hydrolysis Of Cellulose As A Means Of Increasing The Rate Of Enzymatic Hydrolysis By Trichoderma Viride Cellulose" (the work described in the Knappert thesis was done under supervision of the present inventor and there was a reduction to practice of concepts first proposed by the present inventor). The Thompson thesis was shelved in the Feldberg Business and Engineering Library of Dartmouth College, Hanover, New Hampshire on or about Mar. 8, 1978 and the Knappert thesis was shelved in the same library on or about July 18, 1978; as is the practice at said Feldberg Business and Engineering Library, each thesis is shelved, but not cataloged. The theses can be used to augment the present specification, and both are incorporated by reference herein.

Attention is also called to U.S. Pat. Nos. 1,428,217 (Classen); 3,212,932 (Hess et al); 3,525,911 (Funk et al); and 3,939,286 (Jelks).

While the present invention has use in conjunction with other sugars than glucose, the production of glucose is discussed mostly hereinafter. Among other things, conversion of cellulosic material to glucose, and subsequent fermentation to ethanol, is a method to utilize a portion of solid waste or biomass and is, also, a method whereby dependence on petroleum-based fuels can be decreased. Currently, two methods are used for cellulose conversion: acid hydrolysis of the cellulose polymer at high temperature with dilute mineral acid can convert about fifty percent of the potential glucose in the cellulose to glucose in seconds, but by-product formation and high energy requirements presently limit use of that conversion mechanism; enzymatic hydrolysis of cellulose results in the same fifty percent conversion to glucose, but reaction times on the order of forty-eight hours are needed, which limits use of such hydrolysis.

It is an object of the present invention to provide a pretreatment process for cellulosic substrate which enhances subsequent hydrolysis of such substrates to produce sugars.

Another object is to provide a pretreatment process which is particularly well adapted to enhance subsequent enzymatic hydrolysis.

Still another object is to provide a process for producing glucose and/or other sugars.

These and still further objects are addressed hereinafter.

The foregoing objects are achieved, generally, in continuous-flow, pretreatment process for cellulosic substrates to render the substrates more susceptible by hydrolysis to glucose and/or other sugars that comprises the steps of producing a slurry comprising cellulosic materials and water; rapidly heating the slurry to a temperature sufficient that changes occur in the cellulosic structure of the substrate but for a time sufficiently short that no substantial amount of glucose and/or other sugars are formed from cellulose; and quenching the slurry. The objects are further achieved in a process that includes the pretreatment process herein and further includes hydrolysis to produce glucose and/or other sugars.

The Thompson thesis discloses a continuous plug-flow reactor that may be employed to practice the pretreatment of the present invention and further processes herein disclosed, but the pretreatment process is not disclosed in the Thompson thesis. The process described in greatest detail in the Thompson thesis concerns acid hydrolysis whereby cellulosic substances or substrates can be hydrolyzed in dilute aqueous acid (about 1% acid) slurries to sugars but with the unavoidable formation of sugar decomposition products. At high temperatures, 230°–240° C., the reaction is fast enough to be complete in one minute or less and give 50–55% yields of the potential glucose. However, about 25% of the sugar produced is lost as decomposition products of sugar, with approximately 25% of the potential yield remaining as unreacted cellulose.

On the other hand the use of cellulase enzymes for the hydrolysis of cellulosic materials, as above indicated, is slow; at least forty-eight hours are needed for finely-milled material to achieve about 50% yield of the potential glucose of the substrate. However, enzymatic hydrolysis has the advantage that only sugars and no undesirable decomposition products of sugars or lignin are formed. In principle, one can achieve quantitative yields if one is willing to go beyond an economic reaction time.

The present inventor has discovered that both forms of hydrolysis (i.e., enzymatic hydrolysis and acid hydrolysis) can be enhanced by pretreatment of the cellulosic substrate. As this explanation unfolds, it will become apparent that two pretreatment mechanisms are employed; which is used depends to a great extent on the economics of a particular system and that, in turn, often depends on local conditions at the site of operation. The first to be explained pretreatment mechanism involves very short-time, high-temperature exposure of the substrate being pretreated to dilute mineral acid hydrolysis; the second pretreatment mechanism involves a short-time, high-temperature treatment of the substrate (with no other acid being added) whereby the natural organic acids of the substrate react with the substrate.

Turning now to the first pretreatment method, dilute acid hydrolysis is used as a partial hydrolysis of the cellulosic substrate. The reaction conditions are achieved by maintaining the temperature in the range between about 180°–230° C. and maintaining the acid concentration and reaction time such that structural changes in the cellulose are made which render it more reactive to enzymatic hydrolysis by cellulase but little or no glucose is formed and/or no significant recrystallization of the cellulose structure occurs.

The key feature here is that the acid pretreatment is done in a short time period, of the order of one minute or less (typically about 0.2 of a minute), and that minimum of free glucose is formed; consequently, little or no sugar decomposition products are formed. This short contact, high-temperature process gives a significantly different effect to the treated substrate than acid hydrolysis of cellulose at low temperatures and longer times. For example, boiling a sample in the mineral acid HCl for three hours at 110° C. makes cellulose residue more crystalline and less reactive to subsequent enzymatic hydrolysis than the original substrate.

In this invention, a continuous plug flow reactor is used which allows rapid heating and acidification of the slurry, controlled reaction time by choosing the correct flow rate and length of the reactor, and rapid quenching of the pretreated slurry by flash cooling (e.g., by exhausting the slurry through a capillary or orifice as shown in the Thompson thesis). The short reaction time and rapid cooling allows the reduction in the degree of polymerization of the cellulosic material, but does not permit the recombination of these cellulose chains. The structural changes are not limited to the reduction in degree of polymerization, but also includes significant removal of hemi-cellulose, which is washed out during the pretreatment, as well as changes in the cellulose lignin bonding. All of these effects together cause the pretreated substrate to have a significantly increased rate of enzymatic hydrolysis and consequently higher glucose yield. For example, enzymatic hydrolysis of oak chips milled to 60 mesh gives 20% glucose yield in forty eight hours with cellulase; whereas an oak sample, pretreated by the present process, gives quantitative yields of glucose in forty-eight hours (see Table I later). Similar results are achieved by other cellulosic materials such as newsprint, poplar and corn stover, for example.

The schematic features of the reactor for acid pretreatment are shown in the Thompson thesis. The main features that are essential to the present process are a continuous flow of cellulosic slurry which is provided by a positive displacement moving cavity pump or screw. The higher the solids concentration the more attractive the economics of the process. The slurry must be acidified and heated to the treatment temperature. This is done in one of two ways. (1) The slurry is heated without acid by a conventional heat exchanger or external heater. No cellulose hydrolysis of any significance occurs during this heat up (in the relatively short time of elevated temperature) without the presence of the acid. Once the slurry is at the desired reaction temperature, a concentrated stream of acid (usually sulfuric acid is used since it is the cheapest, but any mineral acid will do) is continuously injected into the hot slurry so that it is rapidly mixed into the slurry in a special mixing tee, giving a final acid concentration in the aqueous phase between 0 to 1%. This method works for slurries in the range of 5-10% solids. (2) The second method is first to add the acid to the cellulose slurry, permitting it to mix completely and penetrate the substrate over a convenient time frame. At low temperature no significant hydrolysis takes place. Next the acid slurry is heated to the desired reaction temperature in the shortest time possible which is of the order of one second by live steam injection. It will be noted that the slow rate of heat transfer in a heat exchanger of an acidified slurry would not be adequate since the heat-up time would be a significant part of the total treatment time. In short, the objective is to achieve an isothermal treatment condition. The second approach is suitable for larger cellulosic particles and/or higher slurry concentrations where rapid acid mixing is not possible. In either of the two methods discussed in this paragraph, an elevated pressure can be maintain so that the slurry pressure is in excess of the vapor pressure thereof of the treatment temperature to prevent boiling.

The hot slurry is then held at the desired reaction temperature by controlling the reactor residence time which is of the order of one minute or less. The reaction is quenched (which arrests the hydrolysis of the cellulose bonds) by the rapid cooling caused by the adiabatic flashing promoted by the continuous pressure drop of the slurry from the reactor through an orifice or capillary. It is desirable to use as large a cellulose particles in the slurry as practical for economic reasons. The limit of the maximum particle size is governed by the diameter of the orifice or capillary in the blowdown section.

The recovered slurry can be neutralized and enzymatically hydrolyzed or it may be filtered to separate the liquid phase from the solid phase before the solids are enzymatically hydrolyzed. The removal of the liquid phase will remove the majority of the hemicellulose sugars in the original substrates.

The second pretreatment process referred to above can be carried out with no acid added to the slurry, merely using the natural acidity components (i.e., the natural organic acids) available in the substrate at these temperatures. This second pretreatment can be effected at a reaction temperature in the range from about 180° C. to 300° C. for a period of time respectively in the range from about five minutes to a fraction of minute; following reaction the slurry is quenched. The degree of enhancement in the rate of enzymatic hydrolysis increases with increasing acid concentration and/or temperature, but under certain circumstances pretreatment with no acid addition will be adequate as just indicated.

A specific example is given below for oak chips which contain 0.418 mg of potential glucose per gram of dry oak. The chips were ground in a Wiley mill to pass through a 60 mesh screen. The material was made up into water slurry with a concentration of 51.26 mg/ml. A well-mixed sample of 50 milliliters of the slurry was taken as the control for subsequent enzymatic hydrolysis. The remaining slurry was processed through a plug flow reactor at the following steady state conditions: Temperature 189° C., residence time of 0.22 minutes and the acid addition was adjusted to give three different pretreatments: 1%, 0.6% and 0.0% (no acid addition).

Fifty milliliter aliquots of the reactor effluent slurry were taken at each acid concentration and neutralized to pH 4.8 with NaOH (any common base will do). The glucose in solution after pretreatment of each slurry was 1.2 mg/ml, 0.6 mg/ml and 0.2 mg/ml respectively for the 1.0%, 0.6% and 0.0% acid concentration. This represents a glucose yield of 5.6%, 2.6% and 0.7%, respectively, for the three acid levels. It should be noted that the glucose yields are low from the pretreatment.

Enzymatic hydrolysis on the neutralized slurries and the control slurry proceeded as follows: A sodium citrate buffer was added to maintain the pH at 4.8 and enzyme was added (cellulose from Trichoderma viride, OM9414 Natick Labs) to give 1 I.U/ml. The total volume of the slurry was adjusted to 100 ml with distilled water. These slurries were placed in a 250 ml flasks which were placed into a shaker bath at 50° C. for 48 hours.

Table I below shows the percent of the potential glucose in solution as determined by a glucose analyzer using glucosidase at 24 and 48 hours and are marked slurry. Another set of enzymatic hydrolyses was carried out on the re-suspended solids obtained by filtering and washing the neutralized slurries. The same enzymatic hydrolysis procedure was followed as in the case of the slurries. The results are also shown in Table I and are marked solids.

It will be noted that without pretreatment the glucose yield is 21.3% in 48 hours. A pretreatment without acid more than doubles this yield. As the acid concentration is increased in the pretreatment, the yield is increased at least four-fold. The yield of the solid residue is always higher than the corresponding slurry.

TABLE I
ENZYMATIC SACCHARIFICATION OF PRETREATED OAK SLURRY AND SOLIDS, PERCENT OF POTENTIAL GLUCOSE

| Pretreatment Conditions | | TIME | |
|---|---|---|---|
| | | 24 Hr. | 48 Hr. |
| 1% acid 189° C. | slurry | 72.1% | 90.4% |
| | solids | 87.4% | 100.0% |
| 0.6% acid 189° C. | slurry | 66.1% | 86.1% |
| | solids | 88.4% | 100.0% |
| 0.0% acid 199° C. | slurry | 34.7% | 45.6% |
| | solids | 42.3% | 54.4% |
| None (control) | | 19.1% | 21.3% |

Preliminary analysis by the present inventor indicates that the pretreatment techniques herein disclosed will enhance subsequent hydrolysis using acid hydrolysis. The approach used to obtain the data will compare the glucose formed in one pass with that in second pass. The approach used to obtain the data will be the following: a substrate slurry will be passed through the reactor at say three temperature levels 180°, 200° and 220° C. with 1% acid. Then the solids from the 220° C. pass will be resuspended into a new slurry and run at 1% acid at 180° C., 200° C. and 220° C. The glucose formed during the second pass will be compared to the corresponding glucose formed for the first pass at the same temperature. It is expected that the second pass solids are more easily hydrolyzed than the original as indicated by the greater amount of glucose formed.

Further modifications of the invention herein disclosed will occur to persons skilled in the art and all such modifications are deemed to be within the scope of the invention as defined by the appended claims.

What is claimed is:

1. A process for pretreating a cellulosic substance, that comprises: preparing a slurry of the cellulosic substance; adding an acid to the slurry to serve as a catalyst; heating the slurry to a reaction temperature at which the cellulose structure of the cellulosic substance is modified by interaction with the acid to a form which is significantly more susceptible to hydrolysis than the untreated substance; maintaining the reaction temperature of the slurry with the acid therein at said temperature for a time period that is long enough for most of the cellulosic substance therein to be modified to said form, said time period being short enough to prevent formation of significant amounts of glucose from cellulose and/or significant recrystallization of the cellulose structure; and quenching the slurry to reduce to insignificance the reaction between the acid and the thusly modified cellulosic substance.

2. A process as claimed in claim 1 wherein the quenching is effected by passing the slurry through a small orifice to achieve rapid withdrawal of energy therefrom by flashing.

3. A process as claimed in claim 1 wherein the heated slurry is maintained at a pressure in excess of the vapor pressure of the slurry at the elevated temperature to prevent boiling.

4. A method of forming glucose that includes the pretreatment process of claim 1 and that includes the further step of introducing the susceptible cellulosic substance thus formed to a hydrolysis process for production of glucose at higher rates than without pretreatment.

5. A method as claimed in claim 4 in which the hydrolysis is enzymatic hydrolysis.

6. A method as claimed in claim 4 in which the hydrolysis is acid hydrolysis.

7. A process as claimed in claim 1 wherein the slurry is aqueous and the acid added is a mineral acid.

8. A process as claimed in claim 7 in which the mineral acid is added when the slurry is at the reaction temperature and quickly and thoroughly intermixed with the cellulosic substance therein, the average residence time of the mineral acid in the slurry at the reaction temperature being short enough to prevent formation of significant amounts of glucose and/or significant recrystallization of the cellulose structure.

9. A process as claimed in claim 7 wherein the reaction temperature is in the range between about 180° C. and 230° C.

10. A process as claimed in claim 7 in which the mineral acid is added to the slurry prior to said heating and at a time when the slurry is at a reduced temperature at which there is insignificant interaction between the mineral acid and the cellulosic substance, the mineral acid and the cellulosic substance in the slurry being thoroughly intermixed to form a substantially homogeneous mixture, and in which said heating of the mixture is very rapid so that said reaction temperature is reached very quickly.

11. A process as claimed in claim 10 in which the average residence time of the mineral acid in the slurry at the reaction temperature is short enough to prevent formation of significant amounts of glucose from cellulose and/or significant recrystallization of the cellulose structure.

12. A process as claimed in claim 7 wherein said time period is no greater than about one minute.

13. A process as claimed in claim 12 wherein said time period is about 0.2 minutes.

14. A process for pretreating a cellulosic substance, that comprises forming an aqueous slurry containing the cellulosic substance; heating the slurry to a reaction temperature in the range from about 180° C. to 300° C. for a period of time respectively in the range from about five minutes to a fraction of a minute; and quenching the slurry.

15. A process for pretreating a cellulosic substance which is to be used as a raw material for making glucose that comprises: forming a slurry containing the cellulosic substance; heating the slurry to a reaction temperature at which a change occurs in the cellulose structure of the cellulosic material that renders the same more susceptible to subsequent hydrolysis to glucose but without forming significant amounts of glucose therefrom; and quenching the slurry to a holding temperature at which there is insignificant further reaction.

16. A continuous-flow pretreatment process for cellulosic substrates to render the substrates more susceptible to hydrolysis to glucose and/or other sugars that comprises the steps of producing a slurry comprising cellulosic materials and water; pumping the slurry to provide a flow thereof and to increase the pressure thereof to one which is at least equal to the vapor pressure of water at the operating temperature; rapidly heating the slurry to a reaction temperature sufficient that changes occur in the cellulosic structure of the substrate, due to a chemical reaction between the slurry and an acid therein, for a time sufficiently short that no substantial amount of glucose and/or other sugars are formed from the cellulose; and quenching the slurry.

17. A method of forming sugars that includes the process of claim 16 and that includes the further step of neutralizing the slurry and of adding enzymes to the slurry to hydrolyze the pretreated substrate to sugar.

18. A method of forming sugars that includes the process of claim 16 and that further includes separating the liquids from the pretreated residue in the slurry and re-suspending the residue with water and enzyme to hydrolyze the pretreated substrate to sugar.

19. A method of forming sugars that includes the process of claim 16 and that further includes separating the liquid of the slurry from solids therein, re-suspending the solids in water and subjecting the re-suspended solids to acid hydrolysis to produce sugar.

20. A continuous-flow pretreatment process as claimed in claim 16 in which quenching is effected by passing the slurry through a small orifice to achieve rapid withdrawal of energy therefrom by flashing to reduce to insignificance the reaction between the acid and the thusly modified cellulosic structure.

21. A continuous-flow pretreatment process as claimed in claim 20 wherein said reaction temperature is in the range between about 180° C. and 230° C.

22. A continuous-flow pretreatment process as claimed in claim 16 wherein said acid is a mineral acid that is added to the slurry in an amount sufficient to provide a dilute acid solution therein.

23. A continuous-flow pretreatment process as claimed in claim 22 wherein the mineral acid in the solution is about one percent or less.

24. A process for pretreating cellulose that comprises: preparing an aqueous slurry of the cellulose; adding an acid to the aqueous slurry in an amount to provide a dilute acid slurry solution; establishing the slurry with the acid therein at a temperature at which the cellulose structure is modified to a form which is significantly more susceptible to hydrolysis than the untreated cellulose and maintaining said temperature for a time period that is long enough for most of the cellulose therein to be modified to said form, said time period being short enough to prevent formation of significant amounts of glucose from cellulose and/or significant recrystallization of the cellulose; and quenching the aqueous slurry to reduce to insignificance the reaction between the acid and the thusly modified cellulose.

25. A process according to claim 24 in which the dilute acid slurry solution is no greater than about 1% acid and the acid is a mineral acid.

26. A process according to claim 24 wherein said temperature is in the range from about 180° C. to 230° C.

27. A process according to claim 24 wherein said temperature is established after the acid has been added to the slurry.

28. A process according to claim 24 wherein the slurry is established to said temperature and then the acid is added and quickly intermixed to provide a homogeneous mixture.

29. A process according to claim 24 in which the slurry is acted upon in a continuous flow system so that the process is a continuous flow pretreatment process and wherein said time period is less than about five minutes.

30. A process according to claim 24 in which said time period is in the range from about 0.2 minutes to about 5 minutes.

31. A process according to claim 24 in which said time period is less than a minute.

32. The product produced by the process of claim 24.

33. A product as defined by claim 32 in which said acid is a mineral acid and in which said temperature is in the range from about 180° C. to 230° C.

34. A product as defined in claim 33 wherein said time period is about one minute or less and in which the amount of mineral acid in the solution is no more than about one percent.

* * * * *